United States Patent [19]

Clauss et al.

[11] 3,968,107
[45] July 6, 1976

[54] PROCESS FOR THE MANUFACTURE OF 6-METHYL-3,4-DIHYDRO-1,2,3-OXATHIAZIN-4-ONE-2,2-DIOXIDE

[75] Inventors: Karl Clauss, Rossert, Taunus; Erwin Schmidt, Kelkheim, Taunus; Hartmut Pietsch, Hofheim, Taunus; Harald Jensen, Frankfurt am Main, all of Germany

[73] Assignee: Hoechst Aktiengesellschaft, Frankfurt am Main, Germany

[22] Filed: July 16, 1975

[21] Appl. No.: 596,247

[30] Foreign Application Priority Data
July 18, 1974 Germany............................ 2434549

[52] U.S. Cl............................................ 260/243 R
[51] Int. Cl.² ....................................... C07D 291/06
[58] Field of Search ............................... 260/243 R

[56] References Cited
UNITED STATES PATENTS
3,917,589   11/1975   Clauss et al......................... 260/243

Primary Examiner—John M. Ford
Attorney, Agent, or Firm—Curtis, Morris & Safford

[57] ABSTRACT

6-Methyl-3,4-dihydro-1,2,3-oxathiazin-4-one-2,2-dioxide and the nontoxic salts thereof are prepared by reacting acetoacetic acid with fluorosulfonyl isocyanate at a temperature of from −20°C to +50°C in the presence of from 0.5 to 2 moles, calculated on the FSI used, of an alkali methal fluoride or a tertiary amine of the formula

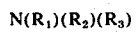

in which $R_1$, $R_2$, $R_3$ represent identical or different alkyl radicals having from 1 to 10 carbon atoms, two of the radicals $R_1$ to $R_3$ optionally form together an alkylene radical having from 4 to 5 carbon atoms which may contain N, O, or S as hetero atom, or one of the radicals $R_1$ to $R_3$ represents a phenyl radical, or of pyridine or quinoline, or of a mixture of the aforesaid compounds, and transforming the salt of acetoacetamide-N-sulfofluoride obtained into the oxathiazinone salt or the free oxathiazinone by a treatment with aqueous and/or alcoholic bases.

8 Claims, No Drawings

PROCESS FOR THE MANUFACTURE OF 6-METHYL-3,4-DIHYDRO-1,2,3-OXATHIAZIN-4-ONE-2,2-DIOXIDE

This invention relates to a process for the manufacture of 6-methyl-3,4-dihydro-1,2,3-oxathiazin-4-one-2,2-dioxide which can be used as sweetener.

U.S. Pat. No. 3,689,486 is concerned with 3,4-dihydro-1,2,3-oxathiazin-4-one-2,2-dioxides, the nontoxic salts thereof, a process for their manufacture and their use as sweetener. The 3,4-dihydro-1,2,3-oxathiazin-4-one-2,2-dioxides are prepared, inter alia, by reacting β-ketocarboxylic acids with fluorosulfonyl isocyanate (FSI) with splitting off of $CO_2$ to obtain β-ketocarboxylic acid amide-N-sulfofluorides which are the subjected to cyclization by a treatment with bases at pH 5 to 12 to yield oxathiazinones. In this manner acetoacetic acid can be reacted with FSI with splitting off of $CO_2$ to yield acetoacetamide-N-sulfofluoride (I) which, in the subsequent treatment with a base in water, is reacted to form the sweetener 6-methyl-3,4-dihydro-1,2,3-oxathiazin-4-one-2,2-dioxide (II) according to the following scheme

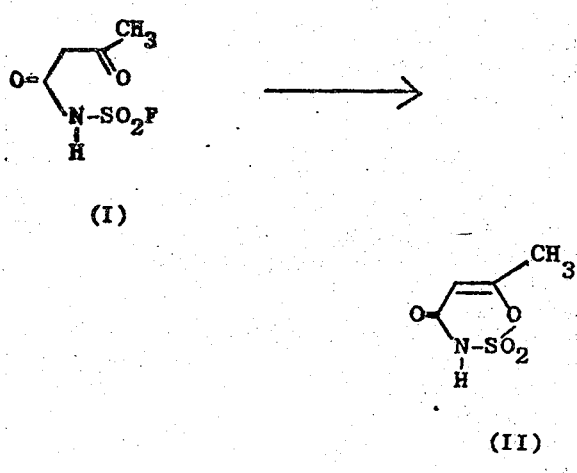

With the use of stoichiometric amounts of the starting components a yield of about 50% of the theory is obtained.

In this reaction, however, the acetoacetamide-N-sulfofluoride (I) is not formed directly but a new heterocyclic compound III is first obtained according to the following reaction scheme

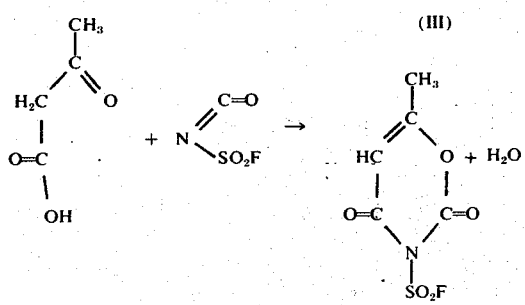

The water formed in this reaction binds a further isocyanate molecule according to the following equation $$H_2O + O=C=N-SO_2F \rightarrow CO_2 + H_2NSO_2F$$

so that the yield of compound I or II, calculated on the isocyanate used, cannot be substantially above 50%. By reacting the heterocyclic compound III with further amounts of water it opens hydrolytically with subsequent splitting off of $CO_2$ to yield the acetoacetamide-N-sulfofluoride (I) from which the oxathiazinone (II) is obtained in known manner.

It has now been found that 6-methyl-3,4-dihydro-1,2,3-oxathiazin-4-one-2,2-dioxide (II) can be prepared from acetoacetic acid and fluorosulfonyl isocyanate, hereinafter designated "FSI", in a much better yield when the reaction is carried out in the presence of compounds forming a complex with FSI, for example a tertiary amine or an alkali metal fluoride.

When FSI is reacted alone with acetoacetic acid only about 50% thereof participate in the oxathiazinone formation while the residual 50% are split to give amidosulfofluoride and $CO_2$. In the presence of a complex forming compound, however, the FSI reacts directly with acetoacetic acid to yield the acetoacetamide-N-sulfofluoride (I) so that yields of the latter compound of 80 – 92% can be readily obtained.

Suitable complex forming compounds for fluorosulfonyl isocyanate are especially alkali metal fluorides (cf. J. A. Roderiguez and R. E. Noftle, Inorganic Chem. volume 10 (1971) page 1874) yielding crystalline 1:1 compounds which are soluble in acetonitrile, for example [KF . FSI], [NaF . FSI] or [CsF . FSI], and tertiary bases which also yield crystalline 1:1 addition products, for example the complexes of FSI with trialkyl amine such as trimethyl, triethyl, tripropyl, tributyl amines, ethyldiisopropyl amine, pyridine, quinoline, or piperazine, morpholine and thiomorpholine.

Therefore, it is the object of the present invention to provide a process for the manufacture of 6-methyl-3,4-dihydro-1,2,3-oxathiazin-4-one-2,2-dioxide (II) and of the nontoxic salts thereof by reacting acetoacetic acid with FSI to yield acetoacetic acid amide-N-sulfofluoride and forming the oxathiazinone ring II, which comprises reacting acetoacetic acid with FSI at a temperature of from −20°C to +50°C in the presence of from 0.5 to 2 moles, preferably 0.9 to 1.2 moles, calculated on the FSI used, of an alkali metal fluoride or a tertiary amine of the formula $$R_1-N-R_2 \atop | \atop R_3$$

in which $R_1$, $R_2$, $R_3$ represent identical or different alkyl radicals having from 1 to 10, preferably 1 to 4 carbon atoms, two of the radicals $R_1$ to $R_3$ optonally form together an alkylene radical having from 4 to 5 carbon atoms which may contain N, O, or S as a hetero atom, or one of the radicals $R_1$ to $R_3$ represents a phenyl radical, or of pyridine or quinoline, or of a mixture of the aforesaid compounds, and transforming the salt of acetoacetamide-N-sulfofluoride obtained into the oxathiazinone salt or the free oxathiazinone (II) by a treatment with aqueous and/or alcoholic bases at a pH of from 5 to 12.

Especially good results are obtained with sodium fluoride, potassium fluoride, or a tertiary amine in which the alkyl radicals have from 1 to 4 carbon atoms each, preferably triethyl amine.

The complex forming compounds are generally used in an amount of from about 0.5 to 2 moles, calculated on 1 mole of FSI used. Higher amounts of up to 5 moles can also be used, but they do not offer any special advantage, as well as amounts below 0.5 mole. The complex forming agents are preferably used in an amount of from 0.8 to 1.5 and more preferably 0.9 to 1.2 moles.

The FSI is preferably used in approximately stoichiometric amounts, calculated on the acetoacetic acid used, or in a slight excess of up to 10%, preferably up to 5%.

The FSI-complex compounds are preferably reacted with acetoacetic acid at such a low temperature that the thermally sensitive acetoacetic acid is not damaged.

The order in which the reaction components and the complex-forming compound are mixed is not critical. The acetoacetic acid can be first mixed with the amine at a temperature suitably below about 30°C, preferably 0° to 20°C, whereupon the FSI is added. Alternatively, the FSI can be first mixed with the complex forming compound and then acetoacetic acid is added, whereby the temperature of the reaction mixture may rise to about 50°C, provided that the acetoacetic acid solution is cooled. Another mode of operation consists in adding the mixture of FSI and complex forming compound to the acetoacetic acid at a temperature of at most about 30°C, preferably of from 0° to 20°C.

The reactions are preferably carried out in solution or suspension. Suitable solvents or diluents are all liquids that are inert towards FSI, preferably those which dissolve acetoacetic acid, for example chlorhydrocarbons such as methylene chloride, chloroform, trichloroethylene; or ethers such as diethyl ether, diisopropyl ether, or tetrahydrofurane. As solvent for the complex compounds of FSI with the alkali metal fluorides acetonitrile is preferred.

The amount of inert solvent to be used is not critical and depends on the practical requirements in each case. In general, the solvent is used in an about 1 to twenty-fold excess by volume calculated on the amount of reactants. Higher or smaller amounts are also possible, the upper limit being determined by economical considerations.

The molar proportion of complex forming compound to FSI is in the range of from 0.5:1 to 2:1, preferably 0.9:1 to 1.2:1.

According to the equation manner, for example as described in the above specification.

Owing to the fact that the salts of the oxathiazinone obtained with inorganic cations, above all the alkali metal salts, and more especially the potassium salt of 6-methyl-3,4-dihydro-1,2,3-oxathiazin-4-one-2,2-dioxide, are sparingly soluble in alcohols, the cyclization to the oxathiazinone can be effected in an especially simple and advantageous manner in an alcohol, for example methanol, ethanol or isopropanol, or in mixtures thereof containing less than 50% by weight of water, preferably less than 20% by weight, with the addition of bases. The oxathiazinone salt of the inorganic base can be isolated practically quantitatively. From the salt the free oxathiazinone can be prepared in known manner without difficulty. It proved particularly advantageous to add methanolic potassium hydroxide, potassium methylate or potassium carbonate solution to the crude acetoacetamide-N-sulfofluoride (II) or to the reaction mixture containing the complex forming compound, optionally after removal of the inert solvent used. The potassium salt of 6-methyl--3,4-dihydro-1,2,3-oxathiazin-4-one-2,2-dioxide separates in the form of crystals and can be filtered off with suction, whilst the potassium fluoride formed essentially remains in solution so that it can be readily separated from the oxathiazine derivative. The ring formation in methanolic potassium hydroxide solution is, therefore, a preferred embodiment of the process of the invention, according to which the oxathiazinone obtained is substantially free from fluoride, which is of extreme importance when the compound is used as sweetener.

For further purification, if any, the crude potassium salt of the oxathiazinone can be recrystallized from boiling water, if necessary with addition of charcoal and filtering aids and obtained in a pure state. An addition of calcium hydroxide promotes the separation of traces of fluoride as insoluble $CaF_2$, which can be readily separated from the solution.

A control of purity of the 6-methyl-3,4-dihydro-1,2,3-oxathiazin-4-one-2,2-dioxide and of its salts is possible by simple UV measurement in dilute solution as the product shows a high absorption maximum at 225 – 228 nm with $\epsilon =$ about $1 \times 10^4$.

The following examples illustrate the invention.

EXAMPLE 1a

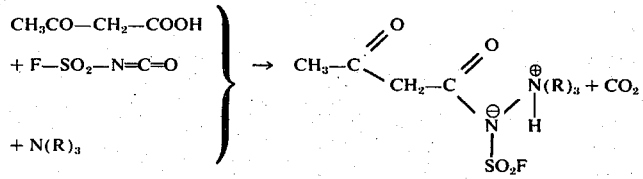

an equivalent amount of $CO_2$ is split off so that the reaction can be readily controlled by volumetric measurement thereof.

With the use of a tertiary amine the amine salt of acetoacetamide N-sulfofluoride (I) is obtained in the first reaction stage and the use of an alkali metal fluoride as complex forming agent yields the corresponding alkali metal salt of (I) as verified by the IR spectra of the products obtained.

The cyclization of compound I or the salts thereof to the oxathiazinone (II) can be carried out in known 51.0 g (0.50 mole) of crystalline acetoacetic acid were dissolved in 250 ml methylene chloride cooled to 0°C and at this temperature 50.5 g (0.50 mole) triethylamine and then 40 ml (0.50 mole) FSI were added dropwise. The isocyanate reacted with vigorous $CO_2$ evolution. After standing for 2 hours the methylene chloride was distilled off under reduced pressure. 140 g of a light yellow oil were obtained which was found according to the IR spectrum to be the triethylamine salt of acetoacetamide-N-sulfofluoride. To bring about cyclization the product obtained was taken up in methanol and immediately thereafter 170 ml 6N alcoholic potassium hydroxide solution was added at 10° – 20°C, the reaction mixture was heated to 30° – 40°C and the crystalline potassium salt of 6-methyl-3,4-dihydro-1,2,3-oxathiazine-4-one-2,2-dioxide was filtered off with suction after cooling to 10°C. The crystals were washed with methanol and dried at 100°C under reduced pressure. 89.5 g of colorless crystals were obtained which were purified and freed of fluoride by recrystallization from boiling water with addition of 1 – 2 g Ca (OH)$_2$. The yield amounted to 85% of the theory.

EXAMPLE 1b

The same result was obtained by adding dropwise a cooled solution of 52.3 g (0.51 mole) of crystalline acetoacetic acid in 160 ml chloroform to a mixture of 100 ml chloroform, 56.4 g (0.56 mole) triethylamine and 41 ml (0.52 mole) FSI at a temperature of −10°C to 0°C. During the course of 60 minutes 12.2 l $CO_2$ were split off. The reaction mixture was further processed as described in the preceding example.

EXAMPLE 2

104 g (1.03 mole) triethylamine and then 80.0 ml (1.0 mole) FSI were added dropwise at 0°C to a solution of 102 g (1.00 mole) acetoacetic acid in 500 ml chloroform whereby about 24 l $CO_2$ were split off. The light yellow oil obtained after distillation of the solvent was taken up in 350 ml methanol and, while stirring and cooling to 20° – 30°C, 290 ml of 7N methanolic potassium hydroxide solution (2.0 moles KOH) were added dropwise. After standing for some time at 0°C the precipitate was filtered off with suction, washed with methanol and dried under reduced pressure. 184 g of white crystals were obtained, i.e. 91.5% of the theory.

To transform the potassium salt into the free acid it was taken up in a mixture of 150 ml water and 500 ml ethyl acetate and, while cooling with ice and stirring, 77 ml of 12N hydrochloric acid were added. The ethyl acetate solution was separated, the aqueous phase extracted once more with 300 ml ethyl acetate and the combined extracts were intensly dried with sodium sulfate. After distillation of the ethyl acetate and drying of the colorless crystals obtained under reduced pressure, 139 g (85% of theory) of free oxathiazinone dioxide (II) melting at 119° – 121°C were obtained.

EXAMPLE 3a

A solution cooled to 0°C of 102 g (1.00 mole) acetoacetic acid in 300 ml methylene chloride was added dropwise while stirring to a mixture of 200 ml methylene chloride, 101 g (1.00 mole) triethylamine and 80 ml (1.0 mole) FSI. The mixture was stirred for 1 hour during which about 1.0 mole $CO_2$ escaped. The solvent was then distilled off under reduced pressure, the yellow oil obtained was transformed as described in Example 1 into the potassium salt of 6-methyl-3,4-dihydro-1,2,3-oxathiazin-4-one-2,2-dioxide. The yield amounted to 85% of the theory.

EXAMPLE 3b

The same result was obtained when the order of addition was reversed, i.e. a mixture of 200 ml methylene chloride, 101 g (1.00 mole) triethylamine and 80 ml (1.0 mole) FSI was added dropwise to the acetoacetic acid solution cooled to 0°C.

EXAMPLE 4a

At a reaction temperature of 40° – 45°C a solution of 51 g (0.50 mole) of crystalline acetoacetic acid in 100 ml chloroform having a temperature of 0°C was added dropwise to a mixture of 100 ml chloroform, 60 g (0.59 mole) triethylamine and 40 ml (0.5 mole) FSI. During the course of 1 hour 12.1 l $CO_2$ were split off. The solvent was then distilled off under reduced pressure and the oil obtained was transformed in methanolic solution and with methanolic potassium hydroxide solution into the potassium salt of 6-methyl-3,4-dihydro-1,2,3-oxathiazin-4-one-2,2-dioxide. Yield 78 g = 77.5% of theory.

EXAMPLE 4b

The reaction of Example 4a was carried out at 20° – 25°C with the same result.

EXAMPLE 5

86 g (0.85 mole) of triethylamine and then 80 ml FSI were added dropwise at 0°C to a solution of 102 g (1.00 mole) acetoacetic acid in 200 ml chloroform. During the reaction 23.0 l of gas were separated. The reaction product was processed as described in Example 1 and 165 g (82% of theory) of potassium salt of 6-methyl-3,4-dihydro-1,2,3-oxathiazin-4-one-2,2-dioxide were obtained.

EXAMPLE 6a

A mixture of 150 ml chloroform, 130 ml tri-n-butylamine and 40 ml (0.50 mole) FSI was added dropwise at 0° – 10°C to a solution of 51.0 g (0.50 mole) acetoacetic acid in 100 ml chloroform. After the addition the temperature was allowed to rise to 25°C. The solution obtained after termination of the $CO_2$ development was freed of the solvent under reduced pressure and the residue was transformed into the potassium salt in methanolic solution with methanolic potassium hydroxide solution (1.0 mole). After recrystallization from boiling water, optionally after addition of 1 – 2 g of calcium hydroxide, 72 g (71.5% of theory) of the pure potassium salt of 6-methyl-3,4-dihydro-1,2,3-oxathiazin-4-one-2,2-dioxide were obtained.

EXAMPLE 6b

When the tri-n-butylamine was replaced by 45 ml pyridine, 68 g (67.5% of theory) of the potassium salt were obtained.

EXAMPLE 6c

When the tributylamine of example 6a was replaced by 77 g (0.60 mole) ethyl-diisopropylamine, 64 g (63.5% of theory) of the potassium salt were obtained.

EXAMPLE 7

A solution of 28.5 g (279 mmoles) crystalline acetoacetic acid in 100 ml chloroform was added at 0° – 10°C to a suspension of 52 g of the crystalline complex (J. F. Roderiguez and R. E. Noftle loc. cit.) of FSI and potassium fluoride (285 mmoles) in 100 ml chloroform. Stirring of the reaction mixture was continued for 2 hours while the temperature was allowed to rise slowly to room temperature. 6.7 l $CO_2$ separated. After distillation of the chloroform under reduced pressure, 68 g of a colorless pulverulent mass were obtained, which according to the IR spectrum essentially consisted of the potassium salt of acetoacetamide-N-sulfofluoride. The mass was taken up in cold methanol (0°C) and while cooling 90 ml of 6N methanolic potassium hydroxide solution were added dropwise. The mixture was stirred for 1 hour at 40°C, cooled to 20°C, the precipitate was filtered off with suction and the white crystals were carefully washed with methanol. Yield 40.2 g of the potassium salt of 6-methyl-3,4-dihydro-1,2,3-oxathiazin-4-one-2,2-dioxide (71.5% of theory).

EXAMPLE 8a 40 ml (0.50 mole) FSI were added dropwise while cooling with ice to a suspension of 32.0 g (0.55 mole) of dry potassium fluoride in 100 ml dry acetonitrile, whereby the potassium fluoride dissolved (cf. J. F. Roderiguez and R. E. Noftle loc. cit.), the internal temperature of the mixture being kept at 20° – 30°C. The mixture was then cooled to 10°C and at an internal temperature of 10° – 20°C a solution of 51 g (0.5 mole) pure acetoacetic acid in 100 ml chloroform was added dropwise. During the course of about 30 minutes 12 l $CO_2$ were collected and white crystals separated. An IR spectrum of the precipitated salt showed that it consisted essentially of the potassium salt of acetoacetamide-N-sulfofluoride. The solvent was distilled off under reduced pressure, the residue was taken up in cold methanol (0°). After addition of 100 ml 6N methanolic potassium hydroxide solution (0.6 mole KOH), stirring for 1 hour at 30° – 40°C and suction filtration at 15° – 20°C, 64.4 g of pure potassium salt of 6-methyl-3,4-dihydro-1,2,3-oxathiazin-4-one-2,2-dioxide (64% of theory) were obtained.

EXAMPLE 8b

When 24 g (0.57 mole) of sodium fluoride were used instead of potassium fluoride the free 6-methyl-3,4-dihydro-1,2,3-oxathiazin-4-one-2,2-dioxide was obtained in a 58% yield when the mixture of sodium and potassium salt obtained was transformed into the acid compound melting at 119° – 122°C under the conditions of Example 2 in a mixture of water and ethyl acetate and with the aid of hydrochloric acid.

EXAMPLE 9

40.0 ml (0.5 mole) FSI were slowly added dropwise while cooling with ice to a solution of 51.0 g (0.5 mole) triethylamine in 50 ml methylene chloride and the solvent was distilled off under reduced pressure. The complex compound [FSI × $N(C_2H_5)_3$] obtained in the form of a light crystal magma was recrystallized from hot ethyl acetate. The colorless crystals obtained melted at 93°C. Yield 92% of theory.

Analysis. $C_7H_{15}FN_2O_3S$, m.w. 226.3. Calc: C, 37.15%; H, 6.7%; F, 8.4% N, 12.4%; S, 14.15%. Found: C, 37.1%; H, 6.6%; F, 8.4%; N, 12.5%; S, 13.9%.

IR(KBr): 5.67 $\mu$ / 6.27 $\mu$ / 7.3 $\mu$ / 7.9 $\mu$ / 8.3 $\mu$ / 9.85 $\mu$ / 10.0 $\mu$ / 11.7 $\mu$ / 11.9 $\mu$.

A solution of 10.2 g (0.1 mole) acetoacetic acid in 50 ml chloroform was added dropwise at 10° – 15°C to a solution of 23.0 g (0.1 mole) of the above crystals melting at 93°C in 50 ml chloroform and the mixture was stirred for a further 2 hours at room temperature. 2.3 l $CO_2$ (about 0.1 mole) were split off. After distillation of the solvent and further treatment in methanolic solution with 33 ml 6.2N methanolic potassium hydroxide solution 17.2 of pure potassium salt of 6-methyl-3,4-dihydro-1,2,3-oxathiazin-4-one-2,2-dioxide were isolated (85% of theory).

What is claimed is:

1. In the process for the manufacture of 6-methyl-3,4-dihydro-1,2,3-oxathiazin-4-one-2,2-dioxide and of the nontoxic salts thereof by reacting acetoacetic acid with fluorosulfonyl isocyanate to yield acetoacetic acid amide- N-sulfofluoride and forming the oxathiazinone ring the improvement which comprises reacting acetoacetic acid with fluorosulfonyl isocyanate at a temperature of from −20°C to +50°C in the presence of from 0.5 to 2 moles, calculated on the isocyanate used, of an alkali metal fluoride or a tertiary amine of the formula

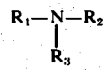

in which $R_1$, $R_2$, $R_3$ represent identical or different alkyl radicals having from 1 to 10 carbon atoms, two of the radicals $R_1$ to $R_3$ optionally form together an alkylene radical which may contain N, O, or S as a hetero atom or one of the radicals $R_1$ to $R_3$ represents a phenyl radical, or of pyridine or quinoline, or of a mixture of the aforesaid compounds, and transforming the salt of acetoacetamide-N-sulfofluoride obtained into the salt of oxathiazinone or the free oxathiazinone by a treatment with an aqueous or alcoholic base or a combination thereof.

2. The process of claim 1, wherein $R_1$, $R_2$, $R_3$ in the amine used represent alkyl radicals having from 1 to 4 carbon atoms and two of the radicals $R_1$ to $R_3$ together optionally form an alkylene radical having 4 or 5 carbon atoms.

3. The process of claim 1, wherein sodium fluoride, potassium fluoride, or triethylamine is used.

4. The process of claim 1, wherein the fluorosulfonyl isocyanate is used in an at least stoichiometric amount.

5. The process of claim 4, wherein the fluorosulfonyl isocyanate is used in an excess of up to 5%, calculated on acetoacetic acid.

6. The process of claim 1, wherein an inert solvent is used.

7. The process of claim 1, wherein the salt of acetoacetamide- N-sulfofluoride is transformed into the oxathiazinone salt by a treatment with an inorganic base in alcoholic solution containing less than 50% by weight water.

8. The process of claim 7, wherein potassium methylate, potassium hydroxide, potassium carbonate, or a mixture thereof in methanolic solution is used and the potassium salt of the oxathiazinone is obtained.

* * * * *